(12) United States Patent
Rosemeyer et al.

(10) Patent No.: US 6,492,176 B1
(45) Date of Patent: Dec. 10, 2002

(54) INCREASE OF NODULE NUMBER AND NITROGEN FIXATION IN LEGUMINOSAE

(75) Inventors: Viola Rosemeyer, Wavre (BE); Jozef Vanderleyden, Heverlee (BE)

(73) Assignee: K.U. Leuven Research & Development, Leuven (BE)

( * ) Notice: Subject to any disclaimer, the term of this patent is extended or adjusted under 35 U.S.C. 154(b) by 0 days.

(21) Appl. No.: 09/582,379

(22) PCT Filed: Dec. 22, 1998

(86) PCT No.: PCT/EP98/08534

§ 371 (c)(1),
(2), (4) Date: Oct. 10, 2000

(87) PCT Pub. No.: WO99/33966

PCT Pub. Date: Jul. 8, 1999

(30) Foreign Application Priority Data

Dec. 23, 1997 (EP) .............................. 97204088
Feb. 17, 1998 (EP) .............................. 98200498

(51) Int. Cl.[7] .......................... C12N 15/74; C12N 1/20; C07H 21/02
(52) U.S. Cl. ................. 435/471; 435/252.2; 435/252.1; 536/23.7
(58) Field of Search .............................. 435/471, 252.2, 435/252.3; 71/7; 536/23.7

(56) References Cited

PUBLICATIONS

Schripsema et al. Bacteriocin dmall of *Rhizobium leguminosarum* Belongs to the Class of N–Acyl–L–Homoserine Lactone Molecules, Known as Autoinducers and as Quoram Sensing Co–Transcription Factors Journal of Bacteriology Jan. 1996 p. 366–371.*

Gray et al. Cell–to–Cell Signaling in the Symbiotic Nitrogen–Fixing Bacterium *Rhizobium leguminosarum*: Autoinduction of a Stationary Phase and Rhizosphere–Expressed Genes Journal of Bacteriolgy Jan. 1996 372–376.*

* cited by examiner

*Primary Examiner*—Remy Yucel
*Assistant Examiner*—Konstantha Katcheves
(74) *Attorney, Agent, or Firm*—Webb, Ziesenheim, Logsdon & Orkin & Hanson, P.C.

(57) ABSTRACT

The present invention relates to a new mutant *Rhizobium etli* CNPAF 512 strain, having an inactivated raiI gene. Inactivation of the raiI gene leads to increased nodule number in beans upon inoculation thereof with the mutant strain. Based on this specific strain other strains can be mutated in the similar gene(s) in order to enable nodule increase and nitrogen fixation in other Leguminosae species.

26 Claims, 7 Drawing Sheets

Figure 2:
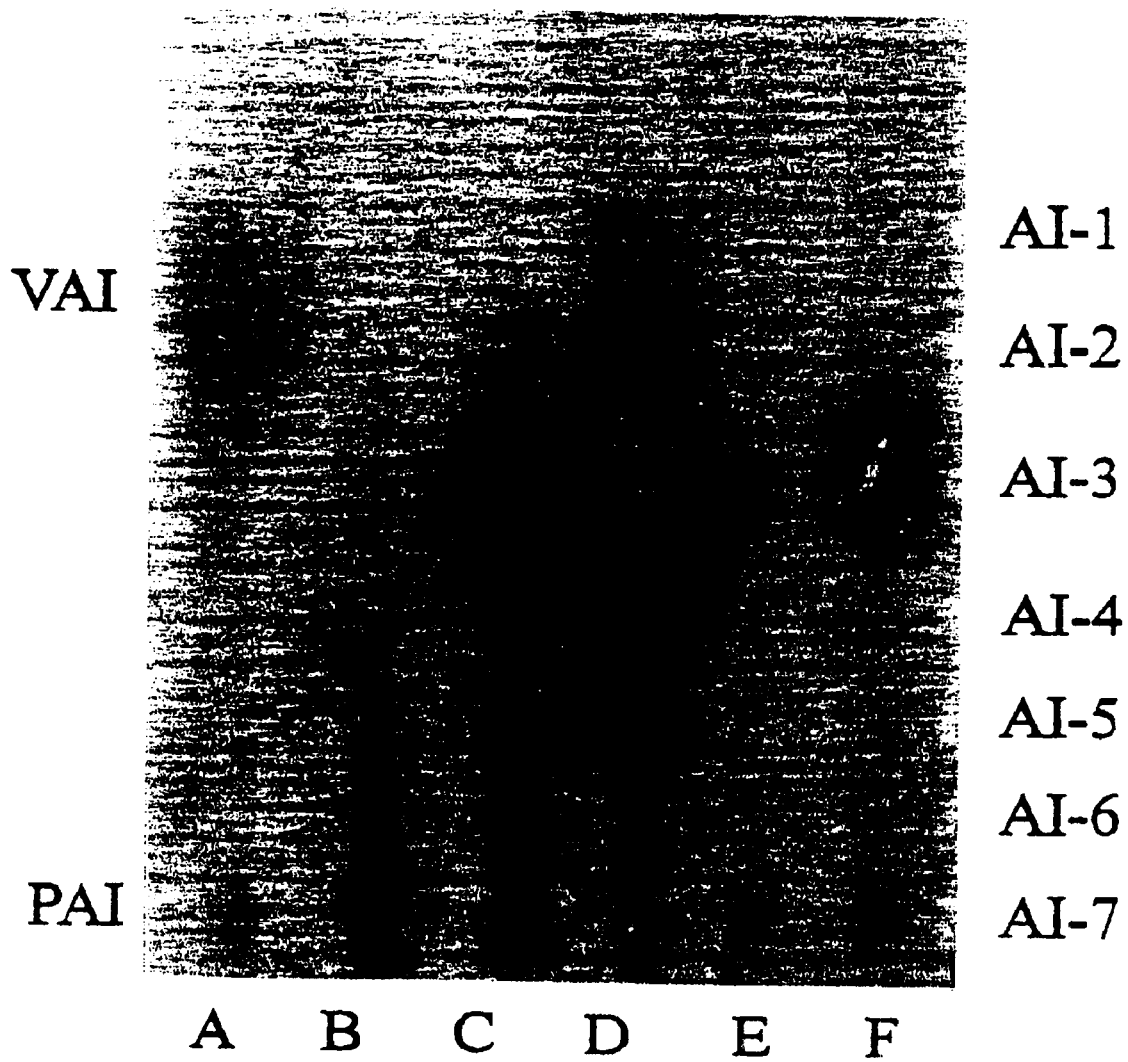

```
         10         20         30         40         50         60
         |          |          |          |          |          |
ATGTTGCGGATACTCACCAAAGACATGCTCGAGACCGATCGACGGGCTTTCGATGAAATG
 M  L  R  I  L  T  K  D  M  L  E  T  D  R  R  A  F  D  E  M 70         80         90        100        110        120
         |          |          |          |          |          |
TTTCGGGCTCGCGCCGCCGTTTTTCGAGATCGTCTGGGATGGCAGGTCGATGTCCGGGAT
 F  R  A  R  A  A  V  F  R  D  R  L  G  W  Q  V  D  V  R  D 130        140        150        160        170        180
         |          |          |          |          |          |
CAATGGGAGAGGGACCGATACGACGAGGCTGAGGATCCCGTCTATCTCGTCACGCAACAA
 Q  W  E  R  D  R  Y  D  E  A  E  D  P  V  Y  L  V  T  Q  Q 190        200        210        220        230        240
         |          |          |          |          |          |
CCTTCCGGCACGCTGACGGGTTCGCTGCGCCTGCTGCCGACCACCGGCGACGATGCTC
 P  S  G  T  L  T  G  S  L  R  L  L  P  T  T  G  A  T  M  L
```

FIG. 1a

```
     250          260          270          280          290          300
      |            |            |            |            |            |
AAAGGCGAGTTCCGGCATTCTTCGATCAGCCTATCGACGTTGATAGCCCGACGACCTGG

K   S   E   F   R   H   F   F   D   Q   P   I   D   V   D   S   P   T   T   W 310          320          330          340          350          360
      |            |            |            |            |            |
GAATGTACCCGCTTTTGCCTTCATCCGCATGCCGGCGATATGAAGCAATCGCCGCAGTC

E   C   T   R   F   C   L   H   P   H   A   G   D   M   K   Q   S   R   A   V
                                                  ‾

370          380          390          400          410          420
      |            |            |            |            |            |
GCCACGGAGCTGCTCTCAGGGCTTTGCGATCTTGCGCTCGACACCGGCATCGAAAACATT

A   T   E   L   L   S   G   L   C   D   L   A   L   D   T   G   I   E   N   I 430          440          450          460          470          480
      |            |            |            |            |            |
GTCGGGGTCTATGACGTCGGCGATGGTCGCGGTGTACCGGAGGATCGGCTGGAGGCCGACG

V   G   V   Y   D   V   A   M   V   A   V   Y   R   R   I   G   W   R   P   T
                          ‾
```

FIG. 1b

```
        490         500         510         520         530         540
         |           |           |           |           |           |
CCGCTTGCCCGATCCCGGCCCGAGATCGGCAAGCTGTATGTTGGTCTATGGGATGTGACG
 P   L   A   R   S   R   P   E   I   G   K   L   Y   V   G   L   W   D   V   T 550         560         570         580         590         600
         |           |           |           |           |           |
GCGGGACAATTGTCGGACACTTAGGGCCAACCTGTCCCGACTTCTGGAGCAAGCCTCTCCC
 A   D   N   C   R   T   L   R   A   N   L   S   R   L   E   Q   A   S   P 610         620         630
         |           |           |
TATCCTGCCAGAGTCCTTGTCGATGGGGGCATGCGATAG
 Y   P   A   R   V   L   V   D   G   G   M   R   -
```

FIG. 1c

```
RaiI  M-LRILTLTKDMLETDRRAFDEMFRARAAVFRDRLGRQVDVRDQWERDRYDE      49
LuxI  MTIMIKKSDFLAIPSEEYKGILSLRYQVFKQRLEWDLVVENNLESDEYDN         50
TraI  MRILTVSPDQYERYRSFLKQMHRLRATVFGGRLENDVSIIAGEERDQYDN         50
RhlI  M-IELLSESLEGLSAAMIAELGRYRHQVFIEKLEGWDVVSTSRVRDQEFDQ        49
      M                              R   VF  L  W         D

RaiI  --AEDPVLVTQQPSGTLTGSLRLLPTTGATMLKSEERHFFDQPIDVDSP         97
LuxI  SNAE---VIYACDDTENVSGCWRLLPTTGDYMLKSVFPELLGQQSAPKD          97
TraI  FKPS---VLLAITDSGRVAGCVRLLPACGPTMLEQTESQLLEMGSLAAHS         97
RhlI  FDHPQTRVIVAMSRQG-ICGCARLLPTTDAYLLKDVEA-YLCSETPPSDE         97
                 Y         G  RLLP       L   F

RaiI  TTWECTRFCLHPHAGDMKQ-S-RAVAFELLS-GLCDLALDTGIENIVGVY        144
LuxI  NIVELSRFAVGKN-SSKINNSASEI-TMKLFEAIYKHAVSQGITEYVTVT        145
TraI  GMVESSRFCVDTSLVSRRDASQLHLAELTLFAGIIEWSMASGYTEIVTAI        147
RhlI  SVWELSRYAASA------ADDPQLAMKIFWSSLQCAWYL-GASSVVAVT         139
          E R                                   G    V

RaiI  DVAMVAVYRRIGWRPTPLARSRPE-IGKLYVGLWDVTADNCRTLRANESR        193
LuxI  STAIERFLKRIKVPCHERIGDKEIHVLGDEKSVVLSMPI-NEQFKKAVEN        193
TraI  DLRFERILKRAGWPMRRLGEPT--AIGNTIAIAGRLPADRASFEQVCPPG        195
RhlI  TTAMERYFVRNGVILQRLGPPQKV-KGEHLVAI-SFPAYQERGLEMLERY        187
                                G

RaiI  LLEQASPYPARVLVDGGMR    212
TraI  YYSIPRIDVAAIRSAA       211
RhlI  HPEWLAEPR              196
```

FIG. 4

SEQUENCE LISTING

<160> NUMBER OF SEQ ID NOS: 8

<210> SEQ ID NO 1
<211> LENGTH: 639
<212> TYPE: DNA
<213> ORGANISM: Rhizobium etli

<400> SEQUENCE: 1

-continued

```
atgttgcgga tactcaccaa agacatgctc gagaccgatc gacgggcttt cgatgaaatg    60
tttcgggctc gcgccgccgt ttttcgagat cgtctgggat ggcaggtcga tgtccgggat   120
caatgggaga gggaccgata cgacgaggct gaggatcccg tctatctcgt cacgcaacaa   180
ccttccggca cgctgacggg ttcgctgcgc ctgctgccga ccaccggcgc gacgatgctc   240
aaaagcgagt tccggcattt cttcgatcag cctatcgacg ttgatagccc gacgacctgg   300
gaatgtaccc gcttttgcct tcatccgcat gccggcgata tgaagcaatc gcgcgcagtc   360
gccacggagc tgctctcagg gctttgcgat cttgcgctcg acaccggcat cgaaaacatt   420
gtcggcgtct atgacgtcgc gatggtcgcg gtgtaccgga ggatcggctg gaggccgacg   480
ccgcttgccc gatcccggcc cgagatcggc aagctgtatg ttggtctatg ggatgtgacg   540
gcggacaatt gtcggacact tagggccaac ctgtcccgac ttctggagca agcctctccc   600
tatcctgcca gagtccttgt cgatggcggc atgcgatag                          639
```

<210> SEQ ID NO 2
<211> LENGTH: 212
<212> TYPE: PRT
<213> ORGANISM: Rhizobium etli

<400> SEQUENCE: 2

```
Met Leu Arg Ile Leu Thr Lys Asp Met Leu Glu Thr Asp Arg Arg Ala
 1               5                  10                  15

Phe Asp Glu Met Phe Arg Ala Arg Ala Val Phe Arg Asp Arg Leu
            20                  25                  30

Gly Trp Gln Val Asp Val Arg Asp Gln Trp Glu Arg Asp Arg Tyr Asp
        35                  40                  45

Glu Ala Glu Asp Pro Val Tyr Leu Val Thr Gln Gln Pro Ser Gly Thr
    50                  55                  60

Leu Thr Gly Ser Leu Arg Leu Leu Pro Thr Thr Gly Ala Thr Met Leu
65                  70                  75                  80

Lys Ser Glu Phe Arg His Phe Phe Asp Gln Pro Ile Asp Val Asp Ser
                85                  90                  95

Pro Thr Thr Trp Glu Cys Thr Arg Phe Cys Leu His Pro His Ala Gly
            100                 105                 110

Asp Met Lys Gln Ser Arg Ala Val Ala Thr Glu Leu Leu Ser Gly Leu
        115                 120                 125

Cys Asp Leu Ala Leu Asp Thr Gly Ile Glu Asn Ile Val Gly Val Tyr
    130                 135                 140

Asp Val Ala Met Val Ala Val Tyr Arg Arg Ile Gly Trp Arg Pro Thr
145                 150                 155                 160

Pro Leu Ala Arg Ser Arg Pro Glu Ile Gly Lys Leu Tyr Val Gly Leu
                165                 170                 175

Trp Asp Val Thr Ala Asp Asn Cys Arg Thr Leu Arg Ala Asn Leu Ser
            180                 185                 190

Arg Leu Leu Glu Gln Ala Ser Pro Tyr Pro Ala Arg Val Leu Val Asp
        195                 200                 205

Gly Gly Met Arg
    210
```

<210> SEQ ID NO 3
<211> LENGTH: 212
<212> TYPE: PRT
<213> ORGANISM: Rhizobium etli -continued

```
<400> SEQUENCE: 3

Met Leu Arg Ile Leu Thr Lys Asp Met Leu Glu Thr Asp Arg Arg Ala
 1               5                  10                  15

Phe Asp Glu Met Phe Arg Ala Arg Ala Ala Val Phe Arg Asp Arg Leu
            20                  25                  30

Gly Trp Gln Val Asp Val Arg Asp Gln Trp Glu Arg Asp Arg Tyr Asp
        35                  40                  45

Glu Ala Glu Asp Pro Val Tyr Leu Val Thr Gln Gln Pro Ser Gly Thr
    50                  55                  60

Leu Thr Gly Ser Leu Arg Leu Leu Pro Thr Thr Gly Ala Thr Met Leu
65                  70                  75                  80

Lys Ser Glu Phe Arg His Phe Asp Gln Pro Ile Asp Val Asp Ser
                85                  90                  95

Pro Thr Thr Trp Glu Cys Thr Arg Phe Cys Leu His Pro His Ala Gly
            100                 105                 110

Asp Met Lys Gln Ser Arg Ala Val Ala Thr Glu Leu Leu Ser Gly Leu
        115                 120                 125

Cys Asp Leu Ala Leu Asp Thr Gly Ile Glu Asn Ile Val Gly Val Tyr
    130                 135                 140

Asp Val Ala Met Val Ala Val Tyr Arg Arg Ile Gly Trp Arg Pro Thr
145                 150                 155                 160

Pro Leu Ala Arg Ser Arg Pro Glu Ile Gly Lys Leu Tyr Val Gly Leu
                165                 170                 175

Trp Asp Val Thr Ala Asp Asn Cys Arg Thr Leu Arg Ala Asn Leu Ser
            180                 185                 190

Arg Leu Leu Glu Gln Ala Ser Pro Tyr Pro Ala Arg Val Leu Val Asp
        195                 200                 205

Gly Gly Met Arg
    210

<210> SEQ ID NO 4
<211> LENGTH: 193
<212> TYPE: PRT
<213> ORGANISM: Vibrio fischeri

<400> SEQUENCE: 4

Met Thr Ile Met Ile Lys Lys Ser Asp Phe Leu Ala Ile Pro Ser Glu
 1               5                  10                  15

Glu Tyr Lys Gly Ile Leu Ser Leu Arg Tyr Gln Val Phe Lys Gln Arg
            20                  25                  30

Leu Glu Trp Asp Leu Val Val Glu Asn Asn Leu Glu Ser Asp Glu Tyr
        35                  40                  45

Asp Asn Ser Asn Ala Glu Tyr Ile Tyr Ala Cys Asp Asp Thr Glu Asn
    50                  55                  60

Val Ser Gly Cys Trp Arg Leu Leu Pro Thr Thr Gly Asp Tyr Met Leu
65                  70                  75                  80

Lys Ser Val Phe Pro Glu Leu Leu Gly Gln Gln Ser Ala Pro Lys Asp
                85                  90                  95

Pro Asn Ile Val Glu Leu Ser Arg Phe Ala Val Gly Lys Asn Ser Ser
            100                 105                 110

Lys Ile Asn Asn Ser Ala Ser Glu Ile Thr Met Lys Leu Phe Glu Ala
        115                 120                 125

Ile Tyr Lys His Ala Val Ser Gln Gly Ile Thr Glu Tyr Val Thr Val
    130                 135                 140
```

```
Thr Ser Thr Ala Ile Glu Arg Phe Leu Lys Arg Ile Lys Val Pro Cys
145                 150                 155                 160

His Arg Ile Gly Asp Lys Glu Ile His Val Leu Gly Asp Thr Lys Ser
                165                 170                 175

Val Val Leu Ser Met Pro Ile Asn Glu Gln Phe Lys Lys Ala Val Leu
                180                 185                 190

Asn

<210> SEQ ID NO 5
<211> LENGTH: 211
<212> TYPE: PRT
<213> ORGANISM: Agrobacterium tumefaciens

<400> SEQUENCE: 5

Met Arg Ile Leu Thr Val Ser Pro Asp Gln Tyr Glu Arg Tyr Arg Ser
1                 5                   10                  15

Phe Leu Lys Gln Met His Arg Leu Arg Ala Thr Val Phe Gly Gly Arg
                20                  25                  30

Leu Glu Trp Asp Val Ser Ile Ile Ala Gly Glu Glu Arg Asp Gln Tyr
            35                  40                  45

Asp Asn Phe Lys Pro Ser Tyr Leu Leu Ala Ile Thr Asp Ser Gly Arg
        50                  55                  60

Val Ala Gly Cys Val Arg Leu Leu Pro Ala Cys Gly Pro Thr Met Leu
65                  70                  75                  80

Glu Gln Thr Phe Ser Gln Leu Leu Glu Met Gly Ser Leu Ala Ala His
                85                  90                  95

Ser Gly Met Val Glu Ser Ser Arg Phe Cys Val Asp Thr Ser Leu Val
                100                 105                 110

Ser Arg Arg Asp Ala Ser Gln Leu His Leu Ala Thr Leu Thr Leu Phe
                115                 120                 125

Ala Gly Ile Ile Glu Trp Ser Met Ala Ser Gly Tyr Thr Glu Ile Val
                130                 135                 140

Thr Ala Thr Asp Leu Arg Phe Glu Arg Ile Leu Lys Arg Ala Gly Trp
145                 150                 155                 160

Pro Met Arg Arg Leu Gly Glu Pro Thr Ala Ile Gly Asn Thr Ile Ala
                165                 170                 175

Ile Ala Gly Arg Leu Pro Ala Asp Arg Ala Ser Phe Glu Gln Val Cys
                180                 185                 190

Pro Pro Gly Tyr Tyr Ser Ile Pro Arg Ile Asp Val Ala Ala Ile Arg
                195                 200                 205

Ser Ala Ala
    210

<210> SEQ ID NO 6
<211> LENGTH: 196
<212> TYPE: PRT
<213> ORGANISM: Pseudomonas aeruginosa

<400> SEQUENCE: 6

Met Ile Glu Leu Leu Ser Glu Ser Leu Glu Gly Leu Ser Ala Ala Met
1                 5                   10                  15

Ile Ala Glu Leu Gly Arg Tyr Arg His Gln Val Phe Ile Glu Lys Leu
                20                  25                  30

Gly Trp Asp Val Val Ser Thr Ser Arg Val Arg Asp Gln Glu Phe Asp
            35                  40                  45

Gln Phe Asp His Pro Gln Thr Arg Tyr Ile Val Ala Met Ser Arg Gln
```

```
                  50                    55                     60
Gly Ile Cys Gly Cys Ala Arg Leu Leu Pro Thr Thr Asp Ala Tyr Leu
65                       70                      75                      80

Leu Lys Asp Val Phe Ala Tyr Leu Cys Ser Glu Thr Pro Pro Ser Asp
                85                      90                      95

Pro Ser Val Trp Glu Leu Ser Arg Tyr Ala Ala Ser Ala Ala Asp Asp
                100                     105                     110

Pro Gln Leu Ala Met Lys Ile Phe Trp Ser Ser Leu Gln Cys Ala Trp
                115                     120                     125

Tyr Leu Gly Ala Ser Ser Val Val Ala Val Thr Thr Thr Ala Met Glu
                130                     135                     140

Arg Tyr Phe Val Arg Asn Gly Val Ile Leu Gln Arg Leu Gly Pro Pro
145                     150                     155                     160

Gln Lys Val Lys Gly Glu Thr Leu Val Ala Ile Ser Phe Pro Ala Tyr
                165                     170                     175

Gln Glu Arg Gly Leu Glu Met Leu Leu Arg Tyr His Pro Glu Trp Leu
                180                     185                     190

Ala Glu Pro Arg
            195

<210> SEQ ID NO 7
<211> LENGTH: 35
<212> TYPE: DNA
<213> ORGANISM: Artificial Sequence
<220> FEATURE:
<221> NAME/KEY:
<222> LOCATION:
<223> OTHER INFORMATION: PCR primer for introducing NotI sites

<400> SEQUENCE: 7
cgcgcggccg ccatagccat cgctggtgat gttgc                              35

<210> SEQ ID NO 8
<211> LENGTH: 36
<212> TYPE: DNA
<213> ORGANISM: Artificial Sequence
<220> FEATURE:
<221> NAME/KEY:
<222> LOCATION:
<223> OTHER INFORMATION: PCR primer for introducing NotI sites

<400> SEQUENCE: 8 cgcgcggccgcatgataggcatcgccgagaaagagg                                36
```

INCREASE OF NODULE NUMBER AND NITROGEN FIXATION IN LEGUMINOSAE

The present invention relates to a new mutant Rhizobium strain that is deficient in a gene involved in autoinducer synthesis. The invention also relates to a method of increasing the nitrogen fixation in Leguminosae and a method of providing a Rhizobium strain having a mutation in a gene involved in autoinducer synthesis and the product of this method.

Autoinduction is a highly conserved mechanism of differential gene expression in many Gram-negative bacteria. The key trigger of this system is the concentration of small diffusible molecules, termed autoinducers in respect to their biological activity. All autoinducers so far identified are N-acyl homoserine lactones (AHLs). They are synthesized by an autoinducer synthase, the product of a luxI-homologous gene, and are thought to bind to a protein belonging to the LuxR-family of transcriptional activators. This autoinducer-protein complex activates the expression of defined genes or sets of genes. As this gene activation occurs only when a required threshold concentration of AHLs is attained, the onset of specific genes is dependent on the cell density of bacteria. Consequently, autoinduction allows bacteria to monitor their own population density and to discriminate between high and low cell density. It can also be understood as a cell-cell communication system.

The physiological processes regulated by autoinduction are diverse, as exemplified by the following systems: bioluminescence in *Vibrio fischeri*, plasmid conjugal transfer in *Agrobacterium tumefaciens*, antibiotic production in *Erwinia carotovora*, and synthesis of exoenzymes in plant and animal pathogens like *E. carotovora* and *Pseudomonas aeruqinosa*. In *Escherichia coli*, a LuxR-homologue is involved in the regulation of cell division.

*Rhizobium etli* CNPAF512 (formerly classified as *R. leguminosarum* bv. *Phaseoli* CNPAF512) forms nitrogen-fixing nodules on the roots of common bean. Within this structure bacteria are densely packed and differentiate into their symbiotic state, the bacteroids, able to reduce atmospheric dinitrogen into ammonia. In view of the high cell density during bacteria-plant interaction, autoinduction may be involved at some stage of symbiosis.

Since the nitrogen-fixation that occurs in the nodules is important for plants, it is always desirable to be able to increase the nitrogen-fixing capacity per plant.

In the research that led to the present invention a *Rhizobium etli* CNPAF512 gene has now been identified by which the Rhizobium strain containing the gene is able to control the number of nodules formed per plant. Based on this information a mutant could be developed in which this particular gene is inactivated and inactivation of this gene led to a significant increase in the number of nodules formed per plant.

The invention thus relates to a new mutant *Rhizobium etli* CNPAF512 strain, in which the biological function of the raiI gene is inactivated. More in particular the invention relates to a mutant *Rhizobium etli* CNPAF512 strain having a gusA-Km insertion in its raiI gene. More in particular, the invention provides a mutant *Rhizobium etli* CNPAF512 strain, herein designated as FAJ1328 and having a gusA-Km insertion in the XhoI restriction site of the raiI gene. The nucleotide sequence of the raiI gene is given in FIG. 1.

Based on the identification of the raiI gene in *Rhizobium etli* CNPAF512 it became possible according to the invention to create other mutant rhizobia strains by:

a) identifying a gene that is at least 40% similar with the raiI gene of *Rhizobium etli* CNPAF512 strain in any rhizobia strain; and b) inactivating the biological function of the gene similar to raiI. In this application the term 'similar' intends to encompass both situations in which sequence homology exists and situations wherein a similar biological function (autoinduction) exists Inactivation of the biological function can be achieved in various ways.

First, the gene similar to raiI can be mutated by either an insertion of any DNA sequence that is capable of disrupting the reading frame or by deletion of a part of the coding sequence, for example also leading to disruption of the reading frame. Mutations that lead to an internal stop codon can also be used to inactivate the biological function.

Second, the biological function of the raiI gene or other genes encoding autoinducer synthases can be inactivated by interfering with their transcription regulation factors. This interference leads to a complete or partial lack of transcription of the raiI gene. "Biological function" is to be understood as comprising both the direct biological function of the gene, i.e. synthesis of the gene product encoded by the gene and the effect thereof, or its indirect biological function, e.g. synthesis of other molecules like autoinducers, the synthesis of which is dependent on the expression of the raiI gene, and the effect of the synthesis of those molecules. For example, for *Rhizobium etli* CNPAF512, one of the ultimate biological functions of the non-mutated raiI gene is limitation of the number of nodules formed upon infection of a species of the Leguminosae.

The rhizobia component of the nodules of Leguminosae is specific at least to the genus of the Leguminosae family members. A skilled person will very well be capable of selecting a suitable rhizobia species for the plant in which the nodule number should be increased. Starting from this rhizobia species mutants can be created in which the biological function of the raiI (homologous) gene or other genes encoding autoinducer synthases is inactivated. The rhizobia encompass inter alia the genus Rhizobium and the genus Bradyrhizobium.

The invention further relates to rhizobia strains being deficient in the biological function of their raiI gene or raiI homologous gene or other genes encoding an autoinducer synthases, obtainable by the method as described above.

According to a further aspect thereof, the invention relates to such mutant rhizobia strains for use in increasing the number of nodules in their corresponding host plants and to a method for increasing the nitrogen fixation in Leguminosae, comprising inoculating Leguminosae plants with a mutant strain and providing circumstances suitable for the rhizobia strain to induce nodules.

In a first preferred embodiment of the invention the Leguminosae plant is a bean plant and the rhizobia strain is a strain modulating bean such as *Rhizobium leguminosarum* biovar phaseoli.

In a second preferred embodiment the Leguminosae plant is a Phaseolus plant and the rhizobia strain is *Rhizobium etli* CNPAF512.

In a third preferred embodiment the Leguminosae plant is a *Glycine max* plant and the rhizobia strain is soy-bean nodulating strain selected from *Bradyrhizobium japonicum* CB1809 and *Bradyrhizobium elkani* BR29W.

According to still a further aspect of the invention there is provided the raiI gene of *Rhizobium etli* CNPAF512 in substantially isolated form, comprising a coding nucleotide sequence that is identical to the coding sequence of the nucleotide sequence depicted in FIG. 1 or at least 90% similar to this sequence, or the complementary sequence of either of these. This raiI gene can be used as a probe for screening other rhizobia strains for the presence of a gene that is at least 40% similar to raiI of *Rhizobium etli* CNPAF512.

The present invention will be further illustrated by the following examples. First it is demonstrated how the presence of the raiI gene was detected through its biological function. Then the relevant genes are isolated (Example 2). Creation of the mutant is described in Example 3, whereas Example 4 illustrates the effect of the mutation on the biological function. Example shows the detection of raiI similar genes in Bradyrhizobium. Example 6 shows mutagenesis of genes encoding autoinducer synthase in other rhizobia species. Example 7 shows the use of raiI as a probe for screening other rhizobia strains.

In the examples reference is made to the following figures:

FIGS. 1A–1C: Nucleotide sequence (SEQ ID NO: 1) of the *R.etli* CNPAF512 raiI gene and deduced amino acid sequence.

FIG. 2: Autoinducers produced by (A) Vibrio fischeri (VAI) and *Pseudomonas aeruginosa* (PAI; purified autoinducers), (B) *E. coli* DH5α, (C) *E. coli* DH5α containing the *R. etli* CNPAF512 raiI and raiR in pUC18 (FAJ1323), (D) *R. etli* CNPAF512 wild type, (E) the *R. etli* CNPAF512 mutant with disrupted raiI (FAJ1328), and (F) the *R. etli* CNPAF512 mutant with disrupted raiR (FAJ1329). Ethyl acetate extracts (B–E) were spotted on a $C_{18}$ reversed phase thin layer chromatography plate. 60% methanol was used as liquid phase. Molecules with autoinducer activity were visualized with a soft agar overlayer containing X-Gal and *A. tumefaciens* indicator cells.

Figure 3:
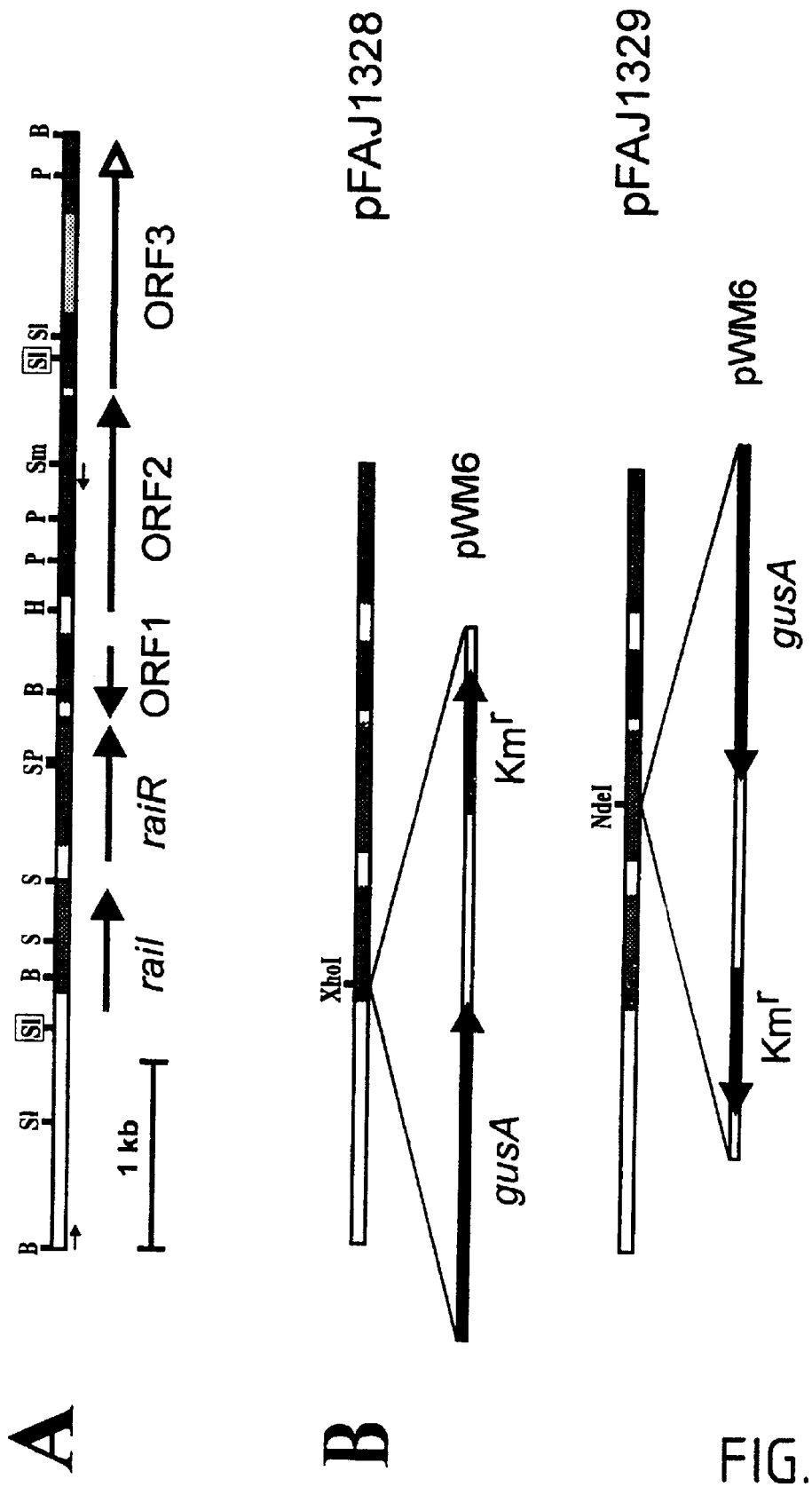

FIGS. 3A and 3B: (A) Physical and genetic map of the region containing raiI and raiR from *R. etli* CNPAF512. Grey shading illustrates coding regions. Arrows indicate directions of transcriptions. The open arrow represents a beginning open reading frame. Light grey color illustrates a part of ORF3 that has not been sequenced. The boxed SalI sites have been used for construction of pFAJ1323. The small arrows indicate the primers with NotI sites used for amplification of a 4 kb fragment. Restriction sites: B, BamHI; H, HindIII; P, PstI; S, SphI; Sl, SalI; Sm, SmaI. (B) Construction of the raiI (FAJ1328) and raiR (FAJ1329) mutant. The PCR product was cloned into pCR™2.1 TA, excised with NotI and inserted into pJQ200uc1. A cassette with a promoterless gusA and kanamycin resistance from pWM6 was introduced in the XhoI (raiI mutant) or NdeI (raiR mutant) site by blunt end ligation.

FIG. 4: Alignments of the members of the LuxI family. A grey background indicates amino acid residues that are identical in at least three aligned sequences. Amino acid residues that are conserved in all the homologues aligned are shown below the sequences. The sequences for RhlI (Accession No. U40458) (SEQ ID NO: 6) and RaiI (Accession No. U92712) (SEQ ID NO: 2) are in the GenBank Sequence Data Library, LuxI (Accession No. P12747) (SEQ ID NO: 4) and TraI (Accession No. P33907) (SEQ ID NO: 5) are in the Swiss-Prot Protein Sequence Database.

Figure 5:
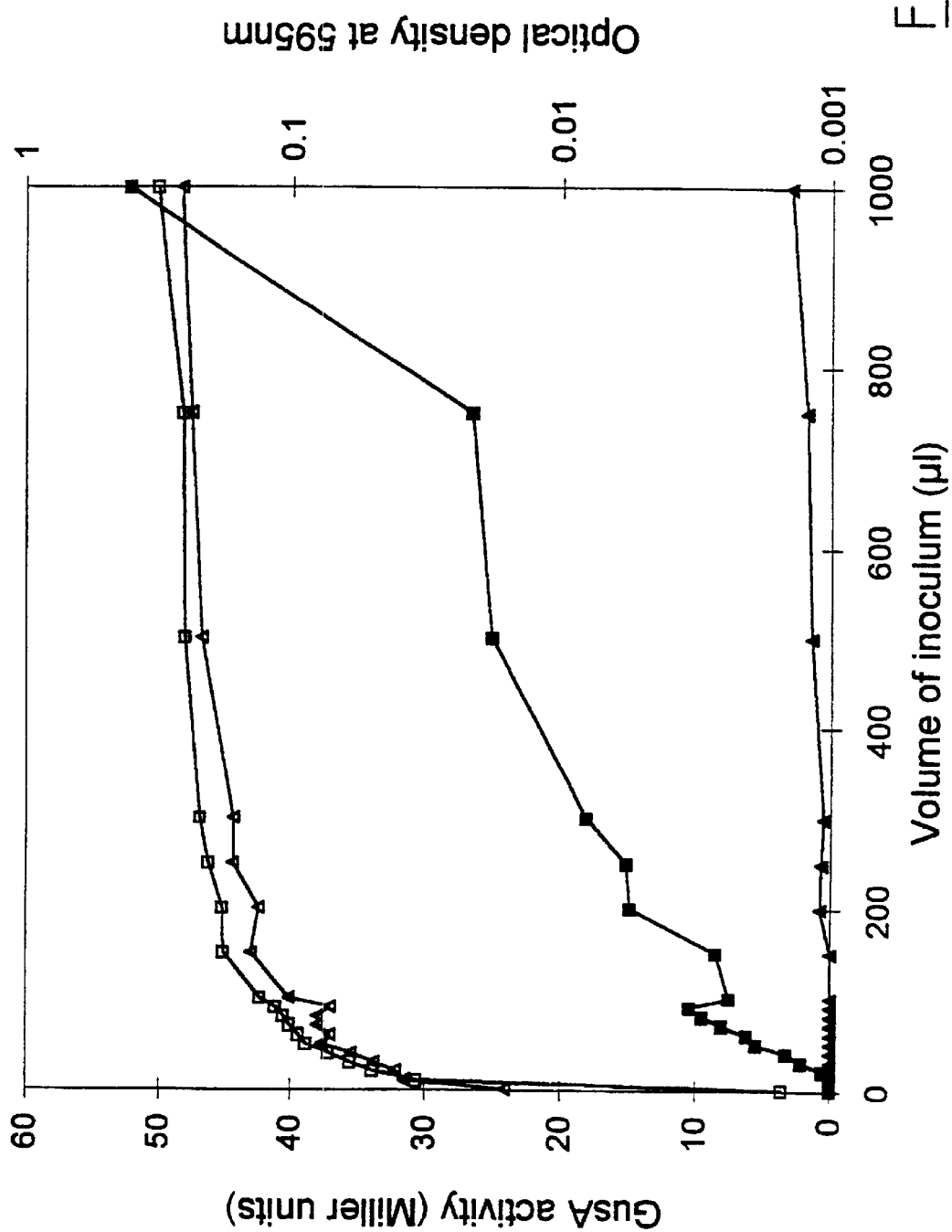

FIG. 5: Comparison of raiI expression in a wild type and raiI mutant background in dependence of cell density. Expression of the raiI::gusA fusions were monitored using p-nitrophenyl-β-D-glucuronide as substrate. Values of optical density and Miller units were based on measurement in microtiter plates. Curves show the averages of three separate experiments. Rectangles represent CNPAF512::pFAJ1328 (raiI::gusA in 3wild type background), triangles FAJ1328 (raiI knockout mutant), open symbols the optical density at 595 nm, and closed symbols GusA activity in Miller units.

EXAMPLES

BACTERIAL STRAINS, PLASMIDS, MEDIA AND CULTURE CONDITIONS

Bacterial strains and plasmids used in these examples are listed in Table 1.

Antibiotic concentrations were as follows: nalidixic acid, 30 μg/ml; ampicillin, 100 μg/ml; kanamycin, 25 μg/ml; neomycin, 60 μg/ml; tetracycline, 10 μg/ml; gentamicin, 25 μg/ml; carbenicillin, 100 μg/ml; rifampicin, 100 μg/ml.

*Escherichia coli* DH5α was grown in LB medium (Sambrook et al., Molecular Cloning—A laboratory manual. Cold Spring Harbor Laboratory Press, Cold Spring Harbor (1989)) at 37° C., *Rhizobium etli* CNPAF512 in TY medium (Beringer, J. Gen. Microbiol. 120: 421–429 (1974)) and A. tumefaciens NT1 (pJM749, pSVB33) in AB medium (Chilton et al., Proc. Natl. Acad. Sci. USA 71: 3672–2676 (1974)) at 28° C.

Example 1

Extraction and detection of autoinducers

*Rhizobium etli* CNPAF512 was grown for 48 h and *E. coli* for 24 h in 500 ml medium to stationary phase. After centrifugation, the supernatant was extracted twice with an equal volume of ethyl acetate containing 1.5 ml acetic acid per litre. The extract was evaporated to dryness by vacuum rotation at 42° C. and redissolved in a small volume of ethyl acetate. 1 μl of this suspension was spotted on a $C_{18}$ reversed phase thin layer chromatography (TLC) plate (RP-18F$_{254s}$, Merck), which was then developed with 60% methanol. The air-dried plate was overlaid with AB soft agar (Chilton et al., supra) containing 5-bromo-4-chloro-3-indolyl-β-galactopyranoside (X-Gal) and *Agrobacterium tumefaciens* NT1 (pJM749, pSVB33) indicator cells (Piper et al., Nature 362: 448–450 (1993), Shaw et al., Proc. Natl. Acad. Sci. USA 94: 6036–6041 (1997)).

This strain contains a Tn3HoHo1-generated lacZ fusion to a tra gene, the expression of which is dependent on TraR and autoinducer. As the clone lacks the Ti plasmid, it does not produce an autoinducer detectable with this system. Consequently, the lacZ reporter fusion is only expressed upon exogenous supply of autoinducer molecules (Piper et al., supra).

Incubation of the TLC plates at 28° C. allowed the visualization of compounds activating the *A. tumefaciens* tra system expression. For comparison, purified autoinducer molecules from *V. fischeri* (VAI, N-(3-oxohexanoyl)-L-homoserine lactone) and from *P. aeruginosa* (PAI, N-(3-oxododecanoyl)-L-homoserine lactone) were used (E. P. Greenberg).

For fractionation, the ethyl acetate extract has been diluted 1:10 with 30% methanol in water, loaded on a $C_{18}$ reversed phase high performance liquid chromatography column (Bondclone 10 C18, Phenomenex) and eluted isocratically with 30% methanol. The fractions were tested for activation of the *A. tumefaciens* tra system and for bacteriostatic activity towards the sensitive strain *R. leguminosarum bv. viciae* 248 as described by Schripsema et al. (J. Bacteriol. 178: 366–371 (1996)).

After *Rhizobium etli* CNPAF512 was grown in 500 ml TY medium for 48h to stationary phase, the ethyl acetate extract of the cell-free spent medium was analyzed on a TLC plate for compounds activating the *A. tumefaciens* tra system expression (FIG. 2D). Seven distinct spots could be detected, indicating, that there are at least seven different autoinducer types present in R. etli CNPAF512. The existence of seven autoinducers in one species is described here for Rhizobium etli CNPAF512 for the first time.

Purified autoinducers from P. aeruginosa (PAI, N-(3-oxododecanoyl)-L-homoserine lactone) and V. fischeri (VAI, N-(3-oxohexanoyl)-L-homoserine lactone) were used for comparison (FIG. 2A). VAI migrated between AI-1 and AI-2 and PAI exhibited similar chromatographic features as AI-7.

The R. etli CNPAF512 ethyl acetate extract has been fractionated on a $C_{18}$ reversed phase high performance liquid chromatography column. Assaying the fractions for tra activation confirmed the presence of at least seven different autoinducer molecules as expected from the results of the TLC plates (data not shown).

After having demonstrated the presence of seven autoinducers in Rhizobium etli CNPAF512, corresponding genes could be identified as described in Example 2.

Example 2

Identification of Autoinducer Encoding Genes

Screening of a 5000 clones comprising R. etli CNPAF512 gene library in Escherichia coli HB101 was performed in microtiter plates. Each 100 µl of AB medium supplemented with 0.003% leucine, 0.023% proline, 0.004% thymine, and 0.0017% thiamine, containing A. tumefaciens indicator cells and X-Gal was pipetted into the wells of a microtiter plate. The clones of the gene library were added, and the plates incubated at 28° C. while shaking.

After 12 h, eight wells were blue. Restriction analysis of the corresponding plasmids and hybridization with a V. fischeri luxI probe from pHV200 (Gray & Greenberg, J. Bacteriol. 174: 4384–4390 (1992)) revealed that they all contained an identical 3.8 kb SalI-fragment. E. coli DH5α containing this SalI-fragment in the pUC18 vector (FAJ1323) could still induce the A. tumefaciens test system to the same extent as the positive E. coli HB101 clones from the library.

Sequencing of pFAJ1323 revealed two open reading frames, the deduced amino acid sequences of which showed similarity to the autoinducer synthases of the LuxI family and to transcriptional activators of the LuxR family. Downstream of these genes are two complete open reading frames and the beginning of a third. The deduced ORF1 protein shows homology to members of the Lrp family of transcriptional regulators (Platko et al., J. Bacteriol. 172: 4563–4570 (1990)). The deduced ORF2 protein shows homology to a catabolic alanine racemase (DadX) and the deduced ORF3 protein shows homology to the small subunit of D-amino acid dehydrogenase (DadA) from E. coli (Lobocka et al., J. Bacteriol. 176: 1500–1510 (1994)). The racemase converts L-alanine to the D isomer, which is then oxidatively deaminated by the D-amino acid dehydrogenase to pyruvate and ammonia (Franklin & Venables, Mol. Gen. Genet. 149: 229–237 (1976)).

FIG. 3A shows the physical map of this region, including the two BamHI fragments, that overlap the 3.8 kb SalI fragment.

The luxI homologous gene, termed raiI (Rhizobium autoinducer synthase), consists of a 639 bp open reading frame that possibly codes for an autoinducer synthase with 212 amino acids (FIG. 1). Sequence similarities of the deduced amino acid sequence with TraI, RhlI and LuxI are relatively low (Table 2). Highest similarities are clustered in the N-terminal region, especially from residue 22 to 36 and from 67 to 84 (referring to RaiI), which is a characteristic feature of LuxI homologues described so far (FIG. 4).

Amino acid residues found to be conserved in 12 LuxI homologues are also present in RaiI (Arg-24, Phe-28, Trp-34, Asp-48, Arg-70, Arg-104). However, instead of a cysteine at position 68 of LuxI, which is thought to be the active site of the autoinducer synthase, RaiI contains a serine.

RaiI is followed by the luxR homologue raiR, separated by 144basepairs. raiR consists of a 729 bp open reading frame and codes for a protein of 242 amino acids. Identities and similarities of RaiR with RhlR, TraR, and RhiR are given in Table 2. The LuxR-related transcriptional activators consist of an N-terminal regulator- and a C-terminal activator domain. Despite of the overall low similarity, the regions for autoinducer binding and the helix-turn-helix motif for DNA binding are conserved.

The organization of raiI and raiR differs from other species, as both are transcribed unidirectionally and the luxI homologue precedes the luxR homologue. In P. aeruqinosa the gene order of the two autoinduction systems (las and rhl) is inversed, in A. tumefaciens traI and traR are not clustered. In all other identified autoinduction systems, both genes are either convergently or divergently transcribed.

The pattern of autoinducers produced by FAJ1323 (FIG. 2B) indicates that RaiI catalyses directly the synthesis of AI-2, AI-3, AI-4, and AI-5. Comparison with the autoinducers synthesized by an raiI mutant (FIG. 2E, see below) indicates, that the spots of AI-3 and AI-5 consist of comigrating molecules. Thus, AI-3 and AI-5 produced by FAJ1323 could be synthesized by RaiI, and the corresponding autoinducers produced by the raiI mutant by other autoinducer synthase(s) than RaiI. The 3.8 kb SalI fragment then was inserted downstream of the lac promoter into the pUC18 vector, which is induced in the presence of isopropyl-β-D-thiogalactopyranoside. However, the synthesis of AI-3 and AI-5 occurs also in the absence of the inducer. It can therefore be concluded that the cloned fragment contained all necessary promoter elements.

Hybridization of total R. etli CNPAF512 DNA in a Southern blot with a raiI probe at low stringency gave rise to only one band.

Example 3

Creation of Mutants

A 4 kb region from pFAJ1322 (cf. description of FIG. 3) comprising raiI, raiR and ORF1, has been amplified by PCR. NotI sites were introduced by designing appropriate PCR primers (5'-CGCGCGGCCGCCATAGCCATCGC TGGTGATGTTGC-3' (SEQ ID NO: 7) AND 5'-CGCGCGGCCGCATGATAGGCATCGGCCGAGA AAGAGG-3') (SEQ ID NO: 8). The product was cloned into the pCR™2.1 TA cloning vector (pFAJ1326). For verification, the terminal regions were sequenced. Subsequently, the fragment was excised with NotI and ligated into pJQ200uc1 (pFAJ1327; Quandt & Hynes, Gene 127:15–21 (1993)).

For mutagenesis of raiI, this construct was linearized with XhoI, allowing the insertion of a promoterless glucuronidase (gusA) gene coupled to a kanamycin resistance gene from pWM6 (Metcalf & Wanner, Gene 129: 17–25 (1993)) at 28 bp downstream of the predicted raiI translation start, resulting in a non-polar-mutation (pFAJ1328; FIG. 3A).

The same cassette was inserted in inversed orientation into raiR via a unique NdeI site, 126 basepairs downstream of the predicted translation start (pFAJ1329; FIG. 3B). These plasmids were conjugated into *R. etli* CNPAF512 with the helper *E. coli* HB101/pRK2013, obtaining cis merodiploid recombinants with a raiI::gusA fusion (CNPAF512::pFAJ1328) or a gusA-Km insertion in raiR. Selection for double homologous recombination using the sacRB-based positive selection system on sucrose (Michiels, Dissertationes De Agricultura, 244 (1993)) led to a raiI mutant with a raiI::gusA fusion (FAJ1328) or a raiR mutant (FAJ1329), respectively. The genotypes of the mutants were verified by hybridization of a raiI-raiR probe and a probe of the pWM6 cassette to the same *R. etli* EcoRI fragment.

In order to examine the phenotypic relevance of raiI and raiR in *R. etli*, spent culture supernatants of the mutants FAJ1328 and FAJ1329 were extracted and analyzed on TLC plates. The chromatogram revealed, that the raiI mutant does not produce AI-1, AI-2, AI-4, and AI-6 in amounts detectable with the assay used (FIG. 2E). AI-3 and AI-5 are produced in a significantly lower amount than in the wild type. The absence of AI-2 and AI-4 confirmed that raiI is directly responsible for the synthesis of these two molecules. The failure of detection of AI-1 and AI-6 suggests, that their synthesis by autoinducer synthase(s) other than RaiI is dependent on autoinducers made by RaiI. In the raiR mutant, four molecules could be detected (FIG. 2F): AI-7 and AI-5 in about the same concentration as in the raiI mutant, AI-3 in higher concentration as in the raiI mutant, and AI-4, which could not be detected in the raiI mutant. AI-1, AI-2, and AI-6 could not be detected, indicating that RaiR is necessary for their synthesis.

raiI expression in a wild type-(CNPAF512::pFAJ1328) and a mutant (FAJ1328) background was examined quantitatively in a cell density dependent way. As shown in FIG. 5, expression of raiI in a wild type background increased with cell density. In the mutant, raiI expression was nearly negligible, indicating that at least one of the autoinducers AI-1, AI-2, AI-4, or AI-6 is necessary for direct or indirect activation of raiI. raiI expression in FAJ1328 was restored in filter sterilized spent medium from *R. etli* CNPAF512. At low cell densities, expression levels in these conditions exceeded those of the wild type in fresh medium (data not shown).

Example 4

Effect of the RaiI Mutation on Nodule Formation

Surface-sterilized and germinated bean seedlings (Van Rijn et al., J. Bacteriol. 175: 438–447 (1993)) were planted under sterile conditions in 0.5 times Jenssen medium (Vincent. A manual for the practical study of root-nodule bacteria. Blackwell Scientific Publications, Oxford/Edinburgh, UK (1970)) and as subsequently inoculated with 200 µl of stationary phase bacterial cultures. The plants were grown at 26° C. for 18 days with 12 h day length. Nitrogen fixation was measured in terms of acetylene reduction by gas chromatography (5890A, Hewlett Packard).

Phenotypic relevance of the rai genes for symbiosis with beans and for nitrogen fixation was examined. Germinated bean seedlings were planted under sterile conditions and subsequently inoculated with 200 µl of dense cultures (OD>1) of *R. etli* CNPAF512, FAJ1328 (raiI mutant), FAJ1329 (raiR mutant), or CNPAF512::pFAJ1334 (merodiploid in respect to raiI and raiR). The plants were grown at 26° C. for 18 days. While no significant difference in delay of the appearance of the first nodules and dry weight of the shoot was observed (Table 3), the number of nodules per plant inoculated with the raiI mutant, FAJ1328, was about twice as high as for the plants inoculated with the wild type. The raiR mutant, FAJ1329, did not differ significantly from the wild type. Inoculation with the merodiploid CNPAF512::pFAJ1334 resulted in a significantly lower acetylene reduction per plant and a reduced nodule number, although a relatively high variation is observed. Values of nodule dry weight and of nitrogen fixation per plant illustrate this observation. However, nitrogen fixing activity in terms of acetylene reduction per nodule remained unchanged. It is therefore concluded that raiI, but not raiR. is involved in the restriction of nodule number, whereas nitrogen fixing activity is not affected. It is further concluded by comparison of the patterns of autoinducers produced by the raiI- and raiR mutant (FIGS. 2E and F), that the molecules representing AI-3, which is synthesized at wild type levels in the raiR mutant but only present in a lower amount in the raiI mutant, or/and AI-4, which could not be detected in the raiI mutant, are involved in the regulation of nodule number.

Example 5

Detection of Autoinducers and the Genes Encoding Autoinducer Synthases in Bradyrhizobium

*B. japonicum* CB1809 and *B. elkani* BR29W were grown for 72 h in PSY medium (per litre: 3 g peptone, 1 g yeast extract, 0.3 g $KH_2PO_4$, 0.3 g $Na_2HPO_4$, 0.01 g $MgSO_4$, 0.01 g $CaCl_2$, 0.01 g $H_3BO_3$, 1 mg $ZnSO_4$ $7H_2O$, 0.5 mg $CuSO_4$ $5H_2O$, 0.1 mg $MnCl_2$ $4H_2O$, 0.1 mg $Na_2MoO_4$ $4H_2O$, 0.16 mg $FeCl_3$ $H_2O$) to stationary phase. After centrifugation, the supernatant was extracted twice with acidified ethyl acetate (1.5 ml acetic acid per litre). The extract was evaporated to dryness by vacuum rotation at 42° C. and then dissolved in a small volume of acidified ethyl acetate. 1 µl of this suspension was spotted on a $C_{18}$ reversed phase thin layer chromatography (TLC) plate (RP-l8F$_{254s}$, Merck), which was then developed with 60% methanol. The air-dried plate was overlaid with AB soft agar (Chilton et al., supra), containing 5-bromo-4-chloro-3-indolyl-β-galactopyranoside (X-Gal) and *Agrobacterium tumefaciens* NT1 (pJM749, pSVB33) indicator cells (Piper et al., supra, Shaw et al., supra). Incubation of the TLC plate at 28° C. allowed the visualization of compounds activating the *A. tumefaciens tra* system expression. For comparison, extract from *R. etli* CNPAF512 was used.

For *B. japonicum* CB1809, three distinct spots could be detected, comigrating with AI-3, AI-4 and AI-5 from *R. etli* CNPAF512. The *B. elkani* BR29W a spot comigrating with AI-3 of *R. etli* CNPAF512 could be detected. For *R. etli* CNPAF512, it has been shown that AI-3 and/or AI-4 are crucial for the regulation of nodule number during symbiosis with its host plant. The presence of autoinducers with identical chromatographic features in both Bradyrhizobium strains show the presence of the same or an analogous regulation system of nodule number in the symbiosis between Bradyrhizobium and its host *Glycine max*.

The above described assay is used to screen a genomic library of Bradyrhizobium in order to find the gene responsible for the synthesis of autoinducer molecules.

Example 6

Mutagenesis of Genes Encoding Autoinducer Synthases in Other Rhizobia Species pFAJ1328, a derivative of the suicide vector pJQ200uc1 (Quandt and Hynes, Gene 127:15–21 (1993)) containing raiI with a gusA-Km$^r$ insertion, raiR and ORF1, has been conjugated to either *B. japonicum* CB1809 or *B. elkani* BR29W with the helper *E. coli* HB101/pRK2073 or *E. coli* HB101/pRK2013, respectively. After selection using appropriate antibiotics ($Ap^{100}$, $Cm^{30}$, $Tc^{150}$, $Km^{150}$ for *B. Japonicum*, $Ap^{100}$, $Cm^{30}$, $Km^{150}$ for *B. elkani*), mutants containing the disrupted raiI gene have been obtained.

Verification is performed by Southern hybridization. In order to knock out the Bradyrhizobium genes similar to raiI, selection for double homologous recombinants is carried out.

Example 7

Use of RaiI as a Probe for Screening Other Rhizobia Strains

The 302 bp SohI fragment from pFAJ1323, containing the region from nucleotide 331 through nucleotide 632 of the raiI gene (see FIG. 1) has been used as hybridization probe for screening other rhizobia strains. Total DNA from *R. leguminosarum* biovar trifolii ANU843 and *R. Leguminosarum* biovar trifolii ATCC 14483 (both can nodulate Trifolium) has been isolated and digested with EcoRI. The fragments have been separated by gel electrophoresis and were subsequently transferred to a nylon membrane. Hybridization was carried out under high stringency (5×SSC, 60° C.). Detection showed that genes similar to raiI are present in the strains tested.

TABLE 1

Bacterial strains and plasmids used in the examples

| Strain or plasmid | Relevant characteristics[a] | Reference or source |
|---|---|---|
| *Escherichia coli* | | |
| DH5α | F⁻Ø80DlacZ ΔM15 endA1 recA1hsdR17 ($r_K^- m_K^-$) supE44 thi-IgyrA96 Δ(lacZYA-argF) | Sambrook et al., Molecular Cloning (1989) |
| HB101 | F⁻hds20 ($r_K^- m_K^-$) supE44 ara14 galK2 lacY1 proA2 rpsL20 Sm$^r$ xyl5 leuB6 mtl1 lambda⁻ recA13 thy thi | Sambrook et al., Molecular Cloning (1989) |
| FAJ1323 | DH5α containing pFAJ1323; Ap$^r$ | present examples |
| *Agrobacterium tumefaciens* | | |
| NTI (pJM749, pSVB33) | Indicator strain for detecting AHLs; Km$^r$, Cb$^r$ | Piper et al., Nature 362:448–450 (1993) |
| *Rhizobium leguminosarum* | | |
| bv. *viciae* 248 | sensitive to bacteriocin "small"; Rif$^r$ | |
| bv. *viciae* RBL 1309 | "small" producing | Van Brussel et al., J. Bacteriol. 162:1079–1082 (1985) |
| bv. *viciae* RBL 1376 | RBL1309 Tn5 mutant; "small"⁻ | Van Brussel et al., J. Bacteriol. 162:1079–1082 (1985) |
| bv. *trifolii* ANU 843 | wild type isolate | |
| bv. *trifolii* ATCC 14483 | wild type isolate | |
| *Rhizobium etli* | | |
| CNPAF512 | Wild-type isolate; Nal$^r$ | Embrapa, Brazil |
| FAJ1328 | raiI::gusA-Km mutant, convergently orientated; Nal$^r$, Km$^r$ | present examples |
| FAJ1329 | raiR mutant, gusA-Km inversely orientated; Nal$^r$, Km$^r$ | present examples |
| CNPAF512::PFAJ1328 | cis merodiploid raiI::gusA-Km; Gm$^r$, Nal$^r$, Km$^r$ | present examples |
| CNPAF512::PFAJ1334 | cis merodiploid ORF1::gusA-Km; two copies of raiI/raiR; Gm$^r$, Nal$^r$, Km$^r$ | present examples |
| Bradyrhizobium | | |
| japonicum CB1809 | wild type isolate | |
| elkani BR29W | wild type isolate | |
| Plasmids | | |
| pHV200 | 8.8 kb SalI fragment with *V. fischeri* ES184 lux regulon; hybridization probe | Gray & Greenberg, J. Bacteriol 174:4384–4390 (1992) |
| pUC18 | ColE1 origin; cloning vehicle; Ap$^r$ | Yanisch-Perron et al., Gene 33:103–119 (1985) |
| pLAFR1 | Incp1 cos oriT; Tc$^r$ | Friedman et al., Gene 18:289–296 (1982) |
| pCR ™ 2.1 TA | ColE1 origin, F1 origin; cloning vehicle for PCR products; Ap$^r$, Km$^r$ | Invitrogen |
| pWM6 | Source of gusA-Km$^r$ cassette; Ap$^r$, Km$^r$ | Metcalf & Wanner, Gene 129:17–25 (1993) |
| pJQ200uc1 | suicide vector, sacB; Km$^r$, Gm$^r$ | Quandt & Hynes, Gene 127:15–21 (1993) |

TABLE 1-continued

Bacterial strains and plasmids used in the examples

| Strain or plasmid | Relevant characteristics[a] | Reference or source |
|---|---|---|
| pRK2013 | ColE1 replicon with RK2 transfer genes; Km$^r$ | Figurski & Helinski, Proc. Natl. Acad. Sci. USA 76:1648–1652 (1979) |
| pFAJ1322 | cosmid clone, pLAFR1 derivative, AHL$^+$; Tc$^r$ | present examples |
| pFAJ1323 | SalI fragment from pFAJ1322 in pUC18; AHL$^+$; Ap$^r$ | present examples |
| pFAJ1326 | PCR fragment (raiI, raiR, ORF1) in PCR ™ 2.1 TA; Ap$^r$ | present examples |
| PFAJ1327 | pCR fragment (raiI raiR, ORF1) in pJQ200ucl via NotI; Gm$^r$ | present examples |
| pFAJ1328 | pFAJ1327; raiI::gusA-Km$^r$, in XhoI; Km$^r$, Gm$^r$ | present examples |
| pFAJ1329 | pFAJ1327; raiR with gusA-Km$^r$ insertion in NdeI; Km$^r$, Gm$^r$ | present examples |
| pFAJ1334 | pFAJ1327; ORF1::gusA-Km$^r$ in BAMHI; Km$^r$, Gm$^r$ | present examples |

[a]Nal$^r$, nalidixic acid resistant;
Ap$^r$, ampicillin resistant;
Km$^r$, kanamycin-neomycin resistant;
Tc$^r$, tetracycline resistant;
Gm$^r$, gentamicin resistant;
Cb$^r$, carbenicillin resistant;
Rif$^r$, rifampicin resistant

TABLE 2

Identities and similarities of LuxI - and LuxR homologues[a]

|  | Tra | RhI | Lux | Rhi |
|---|---|---|---|---|
| RaiI | 28(47) | 25(40) | 23(40) |  |
| RaiR | 18(32) | 22(39) | 17(29) | 17(34) |

[a]The values for the number of identical or identical and similar (in brackets) amino acid residues are given as percentage referring to RaiI or RaiR. References for the sequences: TraI, *A. tumefaciens* (Hwang, J. et al., Proc. Natl. Acad. Sci. USA 91:4639–4643 (1994)); RhII and RhIR, *Pseudomonas aeruginosa* (Brint, J. M. & Ohman, D. E., J. Bacteriol 177:7155–7163 (1995)); LuxI and LuxR, *V. fischeri* (Devine, J. H. et al.) Biochem. 27:837–842 (1988)); TraR, *A. tumefaciens* (Piper, K. R. et al. Nature 362:448–450 (1993)); RhiR, *R. leguminosarum* bv. *viciae* (Cubo, M. T. et al., J. Bacteriol. 174:4026–4035 (1992)).

TABLE 3

Phenotypic characterization of mutants under symbiotic conditions[a]

|  | CNPAF512 | FAJ1328 | FAJ1329 | CNPAF512: :pFAJ1334 |
|---|---|---|---|---|
| appearance of first nodules (d) | 9.1 (1.5)$^A$ | 10.6 (1.8)$^A$ | 10.0 (1.2)$^A$ | 11.6 (1.6)$^A$ |
| shoot dry weight (mg) | 217 (55)$^A$ | 270 (63)$^A$ | 218 (58)$^A$ | 196 (45)$^A$ |
| nodule number | 59.5 (15.3)$^A$ | 118.4 (26.2)$^B$ | 62.8 (17.4)$^A$ | 44.9 (12.3)$^A$ |
| nodule dry weight (mg) | 18.7 (5.6)$^A$ | 31.6 (6.9)$^B$ | 18.1 (4.9)$^A$ | 10.9 (4.1)$^A$ |
| acetylene reduction per plant ($\mu$mol h$^{-1}$) | 3.1 (0.4)$^A$ | 5.1 (0.9)$^B$ | 3.0 (0.4)$^A$ | 1.9 (0.3)$^C$ |
| acetylene reduction per nodule ($\mu$mol h$^{-1}$) | 52.1 (6.7)$^A$ | 43.1 (7.6)$^A$ | 47.8 (6.4)$^A$ | 42.3 (6.7)$^A$ |

[a]Values are based on examination of at least ten plants. The 95% confidence interval is given in brackets. Strains with the same letter are not significantly different for the tested parameter.

What is claimed is:

1. Mutant *Rhizobium etli* CNPAF5812 strain, in which the biological function of the raiI gene is inactivated, which biological function consists of production of one or more autoinducer synthases, and which gene has a nucleotide sequence that hybridizes under stringent conditions to a hybridization probe having the nucleotide sequence which consists of SEQ ID NO: 1 or the complement of SEQ ID NO: 1.

2. Mutant *Rhizobium etli* CNPAF512 strain as claimed in claim 1 having a gusA-Km$^r$ insertion in its raiI gene.

3. Mutant *Rhizobium etli* CNPAF512 strain as claimed in claim 2 and herein designated as FAJ1328, having a gusA-Km$^r$ insertion in the XhoI restriction site of the raiI gene.

4. Method of providing a *Rhizobium etli* CNPAF512 strain having a mutant raiI gene, comprising inactivation of the biological function of the raiI gene, which biological function consists of production of one or more autoinducer synthases, and which gene has a nucleotide sequence that hybridizes under stringent conditions to a hybridization probe having the nucleotide sequence which consists of SEQ ID NO: 1 or the complement of SEQ ID NO: 1.

5. Method as claimed in claim 4, wherein the inactivation of the biological function of the raiI gene comprises insertion of a gusA-Km$^r$ fragment in the XhoI restriction site of the raiI gene.

6. Method for providing a rhizobia strain having a mutant raiI gene, comprising:
   a) identifying in any rhizobia strain a gene that is homologous to the raiI gene of *Rhizobium etli* CNPAF512 strain, which gene has a nucleotide sequence that hybridizes under stringent conditions to a hybridization probe having the nucleotide sequence which consists of SEQ ID NO: 1 or the complement of SEQ ID NO: 1; and
   b) inactivating the biological function, which consists of the production of one or more autoinducer synthases, of the gene having a nucleotide which gene has a nucleotide sequence that hybridizes under stringent conditions to a hybridization probe having the nucleotide sequence which consists of SEQ ID NO: 1 or the complement of SEQ ID NO: 1.

7. Method as claimed in claim 6, comprising:
a) identifying in any rhizobia strain a gene that exhibits at least 40% sequence similarity with the raiI gene of *Rhizobium etli* CNPAF512 strain, which raiI gene has a nucleotide sequence that hybridizes under stringent conditions to a hybridization probe having the nucleotide sequence which consists of SEQ ID NO: 1 or the complement of SEQ ID NO:1; and
b) inactivating the biological function, which consists of the production of one or more autoinducer synthases, of the raiI homologous gene.

8. Method as claimed in claim 6, comprising:
a) identifying in any rhizobia strain a gene that has a similar biological function as the raiI gene of *Rhizobium etli* CNPAF512 strain, which raiI gene has a nucleotide sequence that hybridizes under stringent conditions to a hybridization probe having the nucleotide sequence which consists of SEQ ID NO: I or the complement of SEQ ID NO: 1; and
b) inactivating the biological function, which consists of the production of one or more autoinducer synthases, of the gene sharing sequence similarity with raiI.

9. Method as claimed in claim 4, wherein the biological function of the raiI gene is inactivated by mutation.

10. Method as claimed in claim 9, wherein the mutation leads to either a disruption of the reading frame or an internal stop codon.

11. Method as claimed in claim 10, wherein the mutation is an insertion of any DNA sequence in the coding sequence of the gene, which insertion is capable of disrupting the reading frame.

12. Method as claimed in claim 10, wherein the mutation is a deletion of a part of the coding sequence of the gene and the deletion is capable of disrupting the reading frame.

13. Method as claimed in claim 4, wherein the biological function of the raiI gene is inactivated by interfering with the expression of one or more genes encoding transcription regulation factors involved in the transcription regulation of the raiI gene.

14. Rhizobia strain being deficient in the biological function of its raiI gene, obtainable by the method as claimed in claim 4.

15. Method for increasing the nitrogen fixation in Leguminosae, comprising inoculating Leguminosae plants with a mutant rhizobia strain, in which the biological function of the raiI gene is inactivated, which biological function consists of production of one or more autoinducer synthases, and which gene has a nucleotide sequence that hybridizes under stringent conditions to a hybridization probe having the nucleotide sequence which consists of SEQ ID NO: 1 or the complement of SEQ ID NO: 1 and providing circumstances suitable for the rhizobia strain to induce root nodules.

16. Method as claimed in claim 15, wherein the Leguminosae plant is a bean plant and the rhizobia strain is a strain nodulating bean.

17. Method as claimed in claim 15, wherein the Leguminosae plant is a Phaseolus plant.

18. Method as claimed in claim 15, wherein the Leguminosae plant is a *Glycine max* plant and the rhizobia strain is a soy-bean nodulating strain selected from *Bradyrhizobium japonicum* CB1809 and *Bradyrhizobium elkani* BR29W.

19. raiI gene of *Rhizobium etli* CNPAF512 in substantially isolated form, comprising a coding nucleotide sequence that hybridizes under stringent conditions to a hybridization probe having the nucleotide sequence which consists of SEQ ID NO: 1 or the complement of SEQ ID NO: 1 or a sequence showing at least 90% sequence similarity to this sequence, or the complementary sequence of either of these.

20. raiI gene as claimed in claim 19, wherein the sequence similarity results in the production of one or more autoinducer synthases.

21. Method as claimed in claim 7, wherein the gene sharing sequence similarity with raiI gene is inactivated by mutation.

22. Method as claimed in claim 8, wherein the gene having a nucleotide sequence that hybridizes under stringent conditions to a hybridization probe having the nucleotide sequence which consists of SEQ ID NO: 1 or the complement of SEQ ID NO: 1 is inactivated by mutation.

23. Method as claimed in claim 7, wherein the gene sharing sequence similarity with raiI is inactivated by interfering with the expression of one or more genes encoding transcription regulation factors involved in the transcription regulation of the gene sharing sequence similarity with raiI.

24. Method as claimed in claim 8, wherein the gene having a biological function similar to raiI is inactivated by interfering with the expression of one or more genes encoding transcription regulation factors involved in the transcription regulation of the gene having a nucleotide sequence that hybridizes under stringent conditions to a hybridization probe having the nucleotide sequence which consists of SEQ ID NO: 1 or the complement of SEQ ID NO: 1.

25. Rhizobia strain being deficient in the biological function of the gene sharing sequence similarity with raiI, obtainable by the method as claimed in claim 7.

26. Rhizobia strain being deficient in the biological function of the gene sharing sequence similarity with raiI, obtainable by the method as claimed in claim 8.

* * * * *

UNITED STATES PATENT AND TRADEMARK OFFICE
CERTIFICATE OF CORRECTION

PATENT NO. : 6,492,176 B1  
DATED : December 10, 2002  
INVENTOR(S) : Viola Rosemeyer et al.

It is certified that error appears in the above-identified patent and that said Letters Patent is hereby corrected as shown below:

Column 1,  
Line 32, "*aeruqinosa*" should read -- *aeruginosa* --.

Column 3,  
Line 10, "Example shows" should read -- Example 5 shows --.  
Line 65, "3wild" should read -- wild --.

Column 8,  
Line 7, "but not raiR." should read -- but not raiR, -- (delete period, insert comma).

Column 9,  
Line 10, "Sohl" should read -- Sphl --.

Column 11,  
Table 2, Footnote Line 4, "RhII and RhIR" should read -- RhlI and RhlR --

Column 22,  
Line 26, "rail" should read -- raiI --.

Signed and Sealed this

First Day of July, 2003

JAMES E. ROGAN  
*Director of the United States Patent and Trademark Office*